US00PP21474P2

(12) United States Plant Patent
Bergman

(10) Patent No.: US PP21,474 P2
(45) Date of Patent: Nov. 16, 2010

(54) ***AZALEA* PLANT NAMED 'YBAZ-1892'**

(50) Latin Name: *Rhododendron hybrida*
Varietal Denomination: YBAZ-1892

(75) Inventor: Wendy R. Bergman, Lehigh Acres, FL (US)

(73) Assignee: Aris Horticulture, Inc., Barberton, OH (US)

( * ) Notice: Subject to any disclaimer, the term of this patent is extended or adjusted under 35 U.S.C. 154(b) by 0 days.

(21) Appl. No.: 12/458,165

(22) Filed: Jul. 1, 2009

(51) Int. Cl.
*A01H 5/00* (2006.01)

(52) U.S. Cl. ..... Plt./238

(58) Field of Classification Search ..... Plt./238
See application file for complete search history.

*Primary Examiner*—Susan B McCormick Ewoldt
(74) *Attorney, Agent, or Firm*—C. A. Whealy

(57) ABSTRACT

A new and distinct cultivar of *Azalea* plant named 'YBAZ-1892', characterized by its dark green-colored leaves that do not abscise during the cooling and forcing periods; uniform, outwardly spreading and mounding plant habit; freely branching habit; uniform and freely flowering habit; white-colored flowers with occasional red purple-colored flecks; double flower form; and excellent postproduction longevity with plants maintaining good flower substance for about four to five weeks in an interior environment.

2 Drawing Sheets

Botanical designation: *Rhododendron hybrida.*
Cultivar denomination: 'YBAZ-1892'.

BACKGROUND OF THE INVENTION

The present Invention relates to a new and distinct cultivar of *Azalea* plant, botanically known as *Rhododendron hybrida,* an evergreen greenhouse-forcing type *Azalea*, and hereinafter referred to by the name 'YBAZ-1892'.

The new *Azalea* plant is a product of a planned breeding program conducted by the Inventor in Alva, Fla. The objective of the breeding program is to create new *Azalea* varieties having uniform plant habit, profuse and uniform flowering response, dark green foliage, good foliage retention during the cooling and forcing periods, resistance to *Cylindrocladium* and excellent postproduction longevity.

The new *Azalea* plant originated from a cross-pollination made by the Inventor in January, 1995, in Alva, Fla., of the *Azalea* 'Party Favor', disclosed in U.S. Plant Pat. No. 10,050, as the female, or seed, parent with a proprietary selection of *Azalea* identified as code number 93C-043-018, not patented, as the male, or pollen, parent. The new *Azalea* was discovered and selected by the Inventor as a single flowering plant within the progeny of the stated cross-pollination in a controlled greenhouse environment in Alva, Fla. in May, 1999.

Asexual reproduction of the new *Azalea* plant by terminal cuttings taken in a controlled environment in Alva, Fla. since November, 1999, has shown that the unique features of this new *Azalea* are stable and reproduced true to type in successive generations.

SUMMARY OF THE INVENTION

Plants of the new *Azalea* have not been observed under all possible environmental conditions. The phenotype may vary somewhat with variations in environment such as temperature and light intensity without, however, any variance in genotype. The following traits have been repeatedly observed and are determined to be the unique characteristics of 'YBAZ-1892'. These characteristics in combination distinguish 'YBAZ-1892' as a new and distinct *Azalea* cultivar:

1. Dark green-colored leaves that do not abscise during the cooling and forcing periods.
2. Uniform, outwardly spreading and mounding plant habit.
3. Freely branching habit.
4. Uniform and freely flowering habit.
5. White-colored flowers with occasional red purple-colored flecks.
6. Double flower form.
7. Excellent postproduction longevity with plants maintaining good flower substance for about four to five weeks in an interior environment.

Plants of the new *Azalea* differ from plants of the female parent, 'Party Favor', in the following characteristics:

1. Plants of the new *Azalea* have double flowers whereas plants of 'Party Favor' have semi-double flowers.
2. Flowers of plants of the new *Azalea* are white in color whereas flowers of plants of 'Party Favor' are dark pink in color.

Plants of the new *Azalea* differ from plants of the male parent selection in the following characteristics:

1. Flowers of plants of the new *Azalea* have fewer petaloids than flowers of plants of the male parent selection.
2. Plants of the new *Azalea* have white-colored flowers whereas plants of the male parent selection have light coral-colored flowers.

Plants of the new *Azalea* can be compared to the plants of 'Irish Lace', disclosed in U.S. Plant Pat. No. 11,187. In side-by-side comparisons conducted in Alva, Fla., plants of the new *Azalea* differed from plants of 'Irish Lace' in the following characteristics:

1. Plants of the new *Azalea* were more vigorous and denser than plants of 'Irish Lace'.
2. Plants of the new *Azalea* had double white-colored flowers whereas plants of 'Irish Lace' had single to semi-double hose-in-hose greenish white-colored flowers.

BRIEF DESCRIPTION OF THE PHOTOGRAPHS

The accompanying colored photographs illustrate the overall appearance of the new *Azalea* plant. These photographs show the colors as true as it is reasonably possible to obtain in colored reproductions of this type. Colors in the photographs may differ slightly from the color values cited in the detailed botanical description, which accurately describe the colors of the new *Azalea* plant.

The photograph on the first sheet comprises a side perspective view of a typical flowering plant of 'YBAZ-1892'.

The photograph on the second sheet is a close-up view of a typical flower of 'YBAZ-1892'.

DETAILED BOTANICAL DESCRIPTION

The aforementioned photographs and following observations and measurements describe plants grown in Alva, Fla. with three plants per 15-cm containers, in a polypropylene-covered shade house during the late spring and under commercial production conditions. During the production of the plants, day temperatures ranged from 13° C. to 37° C. and night temperatures ranged from 0° C. to 26° C. Plants were pinched at planting, pinched a second time about twelve weeks later and then pinched a third time about twelve weeks after the second pinch. After sufficient flower bud development, plants were cooled at 3° C. to 5° C. for four weeks to break flower bud dormancy. Plants were subsequently forced into flower under commercial production conditions in a polyethylene-covered greenhouse. Plants used for the photographs and description were one year old. In the following description, color references are made to The Royal Horticultural Society Colour Chart, 2007 Edition, except where general terms of ordinary dictionary significance are used.

Botanical classification: *Rhododendron hybrida* 'YBAZ-1892'.

Commercial classification: Evergreen greenhouse-forcing type *Azalea*.

Parentage:

*Female, or seed, parent.*—*Rhododendron hybrida* 'Party Favor', disclosed in U.S. Plant Pat. No. 10,050.

*Male, or pollen, parent.*—Proprietary selection of *Rhododendron hybrida* identified as code number 93C-043-018, not patented.

Propagation:

*Type.*—By terminal vegetative cuttings.

*Time to initiate roots, summer.*—About five weeks at temperatures of 24° C.

*Time to initiate roots, winter.*—About six weeks at temperatures of 24° C.

*Time to produce a rooted young plant, summer.*—About nine weeks at temperatures of 24° C.

*Time to produce a rooted young plant, winter.*—About eleven weeks at temperatures of 24° C.

*Root description.*—Fine, fibrous, and white in color.

*Rooting habit.*—Freely branching; moderately dense.

Plant description:

*Plant form and growth habit.*—Perennial, evergreen; uniform, outwardly spreading and mounding plant habit; broad inverted triangle; moderately vigorous growth habit; densely foliated; full and bushy plant form; uniform and freely flowering habit with numerous double flowers per plant.

*Branching habit.*—Freely branching habit with about four primary lateral branches develop after the initial pinch (removal of terminal apex); numerous secondary and tertiary branches develop after the sequential second and third pinches.

*Plant height, soil level to top of flowers.*—About 27.5 cm.

*Plant diameter, area of spread.*—About 41.5 cm.

*Lateral branch description.*—Length: About 22.5 cm. Diameter at base: About 4 mm. Internode length: About 1.5 cm. Strength: Strong. Texture, developing: Pubescent, fine brown hairs. Texture, mature: Woody; pubescent, fine brown hairs. Color, developing: Close to 144A. Color, mature: Close to 165A.

*Foliage description.*—Arrangement: Alternate, single. Foliage retention: Very good foliage retention on plants of the new *Azalea* that have been in a box for six weeks during the cooling treatment. Length: About 4.9 cm. Width: About 2.7 cm. Shape: Mostly elliptic. Apex: Mucronate, acute. Base: Attenuate. Margin: Entire. Venation pattern: Pinnate. Texture, upper and lower surfaces: Pubescent; leathery, tough. Color: Developing and fully expanded leaves, upper surface: Darker than 147A; venation, darker than 147A. Developing and fully expanded leaves, lower surface: Close to 147B; venation, close to 146A to 146B. Petiole: Length: About 1.1 cm. Diameter: About 3 mm. Texture, upper and lower surfaces: Pubescent. Color, upper and lower surfaces: Close to 144A to 144B.

Flower description:

*Natural flowering season.*—Spring after sufficient cool period. If forced, plants typically flower about one month after a four-week cooling treatment; relatively rapid flowering response.

*Flower arrangement and appearance.*—Flowers arranged singly at terminals with usually about three flowers per apex; uniform and freely flowering habit, flowers face upward or outward.

*Flower appearance.*—Flowers rotate and rose-like; double flower form with a single outer whorl of five petals and four to five inner whorls of petaloids (transformed reproductive organs).

*Postproduction longevity.*—Excellent postproduction longevity; under interior conditions, plants maintain good flower substance for about four to five weeks; flowers persistent.

*Fragrance.*—None detected.

*Flower diameter.*—About 6.9 cm.

*Flower depth.*—About 3 cm.

*Flower bud (before showing color).*—Length: About 1.3 cm. Diameter: About 6 mm. Shape: Ovoid. Color: Between 146B and 144A.

*Petals/petaloids.*—Arrangement: Double flower form; one outer whorl of five petals and about four to five inner whorls each with about five imbricate petaloids; petals and petaloids fused at the base; petaloids variable in size and shape. Petals: Length: About 3.5 cm. Width: About 3.5 cm. Petaloids, largest: Length: About 3.2 cm. Width: About 2.75 cm. Shape, petals and petaloids: Beyond fused base, roughly spatulate to orbicular with rounded apex. Margin, petals and petaloids: Entire; undulate and ruffled. Texture, petals and petaloids, upper and lower surfaces: Smooth, glabrous; velvety. Color, petals and petaloids: When opening, upper and lower surfaces: Close to NN155C to NN155D. Fully opened, upper and lower surfaces: Close to NN155C to NN155D; occasional random flecks, close to 61B.

*Sepals.*—Arrangement: Five in a single whorl, fused; subtending the petals. Length: About 3 mm. Width: About 2.5 mm. Shape: Rounded deltoid. Apex: Acute. Base: Fused. Texture, upper and lower surfaces: Pubescent. Color, upper surface: Close to 144A. Color, lower surface: Close to 146A.

*Peduncles.*—Length: About 2.1 cm. Diameter: About 2 mm. Angle: Mostly upright. Strength: Flexible; strong. Texture: Pubescent. Color: Close to 144A.

*Reproductive organs.*—None observed, stamens and pistils transformed into petaloids.

*Seed/fruit.*—Seed and fruit development have not been observed.

Weather/temperature tolerance: Plants of the new *Azalea* have been observed to be very tolerant to rain and wind. Plants of the new *Azalea* have been observed to tolerate temperatures from about 0° C. to about 38° C.

Disease/pest resistance: Plants have not been observed to be resistant to pathogens and pests common to *Azaleas*.

It is claimed:

1. A new and distinct cultivar of *Azalea* plant named 'YBAZ-1892' as illustrated and described.

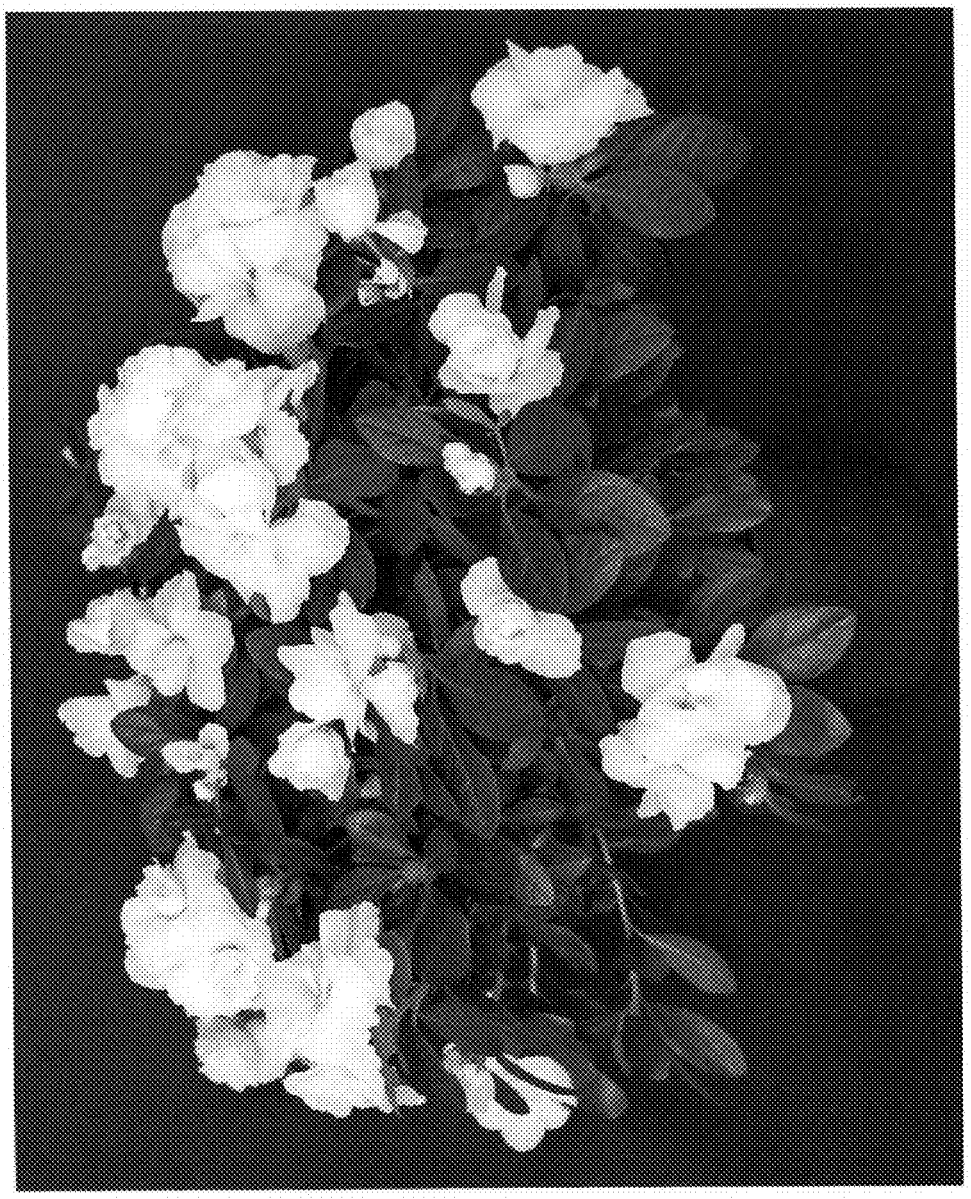

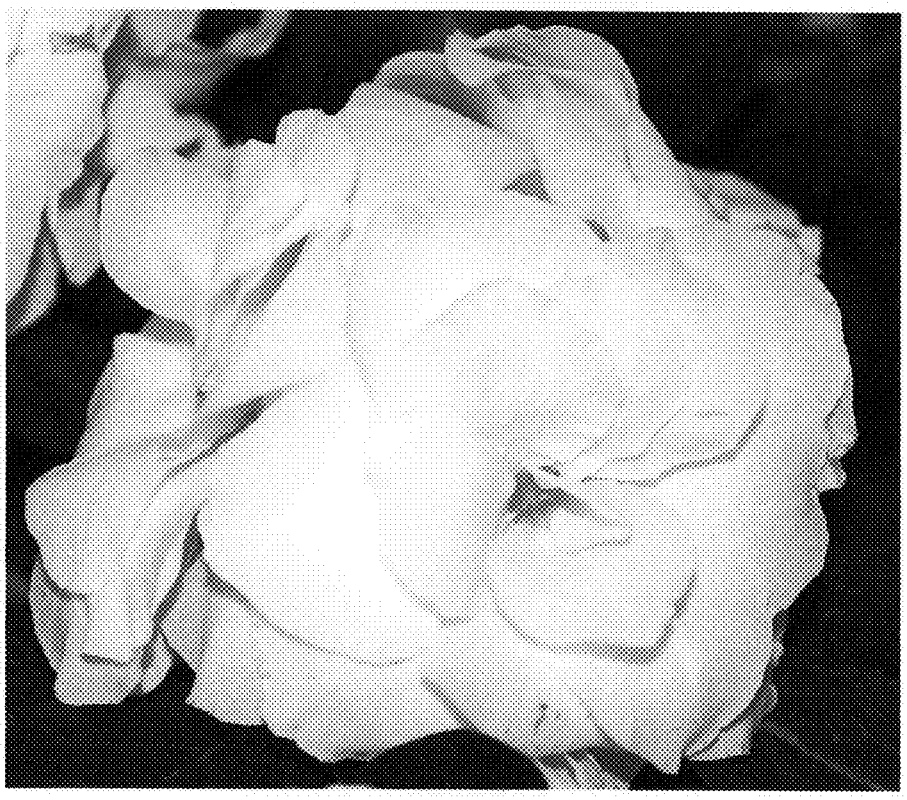

* * * * *